United States Patent [19]

Adams et al.

[11] Patent Number: 5,282,981

[45] Date of Patent: Feb. 1, 1994

[54] FLOW RESTRICTOR-SEPARATION DEVICE

[75] Inventors: George A. Adams, Ottawa, Canada; Robert P. Luoma, II, Newark, Del.

[73] Assignee: E. I. Du Pont de Nemours and Company, Wilmington, Del.

[21] Appl. No.: 877,496

[22] Filed: May 1, 1992

[51] Int. Cl.⁵ .............................................. B01D 21/26
[52] U.S. Cl. ..................................... 210/789; 210/787; 210/800; 210/516; 422/72; 422/101; 73/32 R
[58] Field of Search ................. 210/104, 515, 516, 97, 210/518, 787, 789, 800; 422/72, 101; 73/32 R; 436/177

[56] References Cited

U.S. PATENT DOCUMENTS

| | | | |
|---|---|---|---|
| 3,468,474 | 9/1969 | Shoblom et al. | 233/27 |
| 3,741,400 | 6/1973 | Dick | 210/516 |
| 3,813,031 | 5/1974 | Anderson | 233/26 |
| 3,849,072 | 11/1974 | Ayres | 23/259 |
| 3,852,194 | 12/1974 | Zine, Jr. | 210/83 |
| 3,929,646 | 12/1975 | Adler | 210/359 |
| 3,941,699 | 3/1976 | Ayres | 210/117 |
| 3,957,197 | 5/1976 | Sartory et al. | 233/4 |
| 3,957,654 | 5/1976 | Ayres | 210/516 |
| 4,001,122 | 1/1977 | Griffin | 210/516 |
| 4,021,352 | 5/1977 | Sarstedt | 210/359 |
| 4,038,788 | 4/1978 | Ferrara | 210/516 |
| 4,083,784 | 4/1978 | Zine, Jr. | 210/83 |
| 4,135,883 | 1/1979 | McNeil et al. | 422/72 |
| 4,151,844 | 5/1979 | Cullis et al. | 128/214 R |
| 4,152,269 | 5/1979 | Babson | 210/516 |
| 4,152,270 | 5/1979 | Cornell | 210/516 |
| 4,154,690 | 5/1979 | Ballies | 210/516 |
| 4,202,769 | 5/1980 | Greenspan | 210/83 |
| 4,203,840 | 5/1980 | Stoeppler et al. | 210/83 |
| 4,269,718 | 5/1981 | Persidsky | 210/787 |
| 4,278,202 | 7/1981 | Westberg | 233/27 |
| 4,283,276 | 8/1981 | Grant | 209/155 |
| 4,284,602 | 8/1981 | Kelton et al. | 422/72 |
| 4,285,810 | 8/1981 | Kirkland et al. | 209/155 |
| 4,350,585 | 9/1982 | Johansson et al. | 210/94 |
| 4,350,593 | 9/1982 | Kessler | 210/516 |
| 4,417,981 | 11/1983 | Nugent | 210/209 |
| 4,443,345 | 4/1984 | Wells | 210/782 |
| 4,522,713 | 6/1985 | Nussbaumer et al. | 210/136 |
| 4,530,691 | 7/1985 | Brown | 494/45 |
| 4,534,465 | 8/1985 | Rothermal et al. | 206/443 |
| 4,550,084 | 10/1985 | Nelson et al. | 436/45 |
| 4,557,719 | 12/1985 | Neumann et al. | 494/37 |
| 4,639,316 | 1/1987 | Eldegheidy | 210/416.1 |
| 4,724,317 | 2/1988 | Brown et al. | 250/231 SE |
| 4,828,716 | 5/1989 | McEwen et al. | 210/740 |

FOREIGN PATENT DOCUMENTS 184274 6/1986 European Pat. Off. ..... G01N 33/48

Primary Examiner—Robert A. Dawson
Assistant Examiner—David Reif Snyder

[57] ABSTRACT

A method of partitioning a pre-selected phase of a sample of liquid having a plurality of phases of differing densities, a separation device and a tube containing the separation device. The sample of liquid is placed in a first chamber of a linear tube that is separated from a second chamber by a separation device. The separation device slidably engages the interior surface of the tube in an essentially fluid-tight manner and has an axial orifice on the longitudinal axis of the tube that is in fluid flow communication with a flow-restriction channel. The phases are ordered concentrically by rotating the tube around its longitudinal axis e.g. in an axial centrifuge. The volume of the first chamber is reduced by movement of the separation device within the tube, that phase of the liquid located axially within the first chamber flowing into the axial orifice and passing through the flow-restriction channel into the second chamber. The reduction of the volume of the first chamber is controlled using phase-separation information. The method is useful in separation of blood components.

12 Claims, 7 Drawing Sheets

FLOW RESTRICTOR-SEPARATION DEVICE

FIELD OF THE INVENTION

The present invention relates to a method and apparatus for the separation into phases of a sample of liquid, including colloidal suspensions, having a plurality of phases of differing densities, and for the separation and maintaining of the separation of one phase of the liquid sample from the remainder of the liquid. The invention is particularly useful in the separation of blood into components thereof, especially for purposes of testing and analysis of blood components.

The liquid to be separated is contained in a chamber, typically a tube, containing a separation device. The chamber is rotated, either axially i.e. about its longitudinal axis, or in a conventional centrifuge i.e. about an axis perpendicular to the longitudinal axis, to cause the liquid to separate into distinct phases, during which rotation a separation device is moved through the liquid to physically separate at least one of the phases. The separation device maintains the separation at the conclusion of the rotation and through subsequent handling steps.

BACKGROUND OF THE INVENTION

Diagnostic tests frequently require separation of a patient's whole blood sample into components, especially cellular portions from non-cellular portions e.g. serum or plasma from cells. For instance, plasma is obtained from anticoagulated blood and still contains all of the coagulation proteins, whereas serum is obtained from clotted blood with the bulk of the coagulation proteins being retained with the clot and red blood cells. Samples of whole blood are typically collected by ventipuncture through a special cannula or needle attached to a syringe or an evacuated collection tube. The sample of blood in the form that is to be separated into components is typically drawn, using a needle, through a penetrable self-sealing elastomeric closure or other stopper into an evacuated tube. Separation is then accomplished, e.g. by rotation of the tube in a conventional centrifuge e.g. a swinging bucket or a fixed angle centrifuge, as the different components of the whole blood have different densities, as described in U.S. Pat. No. 4 152 269 of A. L. Babson.

It is frequently desirable to physically isolate the separated phases from each other, so that separation of the phases is maintained after centrifugal rotation has ceased. Isolation may be accomplished by interposing a gel material between the phases, the gel material typically being a silicone that is placed in the tube at the time of manufacture. These gels have densities that are intermediate those of the phases being separated and become interposed between the phases during centrifugal rotation, as is described in U.S. Pat. No. 4 350 593 of Kessler and U.S. Pat. Nos. 3 852 194 and 4 083 784 of A. R. Zine. However, the gels may contain absorbed substances that can interfere with blood analyses or adsorb specific compounds from the blood e.g. tricyclic drugs, the separation of plasma or serum from blood cells may be incomplete and severe jarring or shaking e.g. as in shipping of samples, may disrupt the seal and result in interaction of the separated phases.

U.S. Pat. No. 3 929 646 of S. L. Adler describes a serum separator for use in a centrifuge separation system. The separator is initially positioned at one end of a tube, adjacent to a tube stopper, with the whole blood sample being contained within the tube. When the tube is subjected to centrifugal force, the separator moves away from the stopper and towards the other end of the tube. The separator is designed so as to have a density that is between the densities of two phases of blood, so that when centrifugation is complete, it is positioned between the two phases. The separator has openings to allow the lighter phase of the blood to pass through the separator and allow the separator to move through the blood sample. Thus, a blood sample can be separated into plasma and cell phases that are physically separated. However, the openings may become plugged with clotted blood fractions or conversely permit migration between phases when there is no centrifugal force; in either event effective separation will be lost.

An apparatus and method of separating blood phases by rotation of a tube about its longitudinal axis i.e. axial rotation, are described in U.S. Pat. No. 4 828 716 of J. A. McEwen et al. The blood sample is introduced to the tube through a cap assembly that consists of a pierceable closure and a separator that has a one-way valve. The tube is then rotated about its longitudinal axis; the heavier cellular phase lines the tube wall and thereby separates from the lighter non-cellular (plasma or serum) phase. Once separation has been achieved, an axial probe penetrates the pierceable closure, detaches the separator from the closure and forces the separator down the tube. The axially-located non-cellular phase passes through the separator. An optical sensor is utilized to detect when the cellular phase begins passing into the separator, and to stop movement of the separator. Thus, the two phases are physically separated. However, it is believed that a separator that is more reliable in operation and which may be manufactured in a cost effective manner is required.

A related application of R. P. Luoma filed concurrently herewith is directed to so-called double ended tubes.

SUMMARY OF THE INVENTION

Accordingly, the present invention provides a method of partitioning a pre-selected phase of a sample of liquid having a plurality of phases of differing densities, comprising the steps of:

(a) containing said sample of liquid in a first chamber of a linear tube, said tube having a second chamber that is separated from the first chamber by a separation device, said second chamber being free of the liquid, said separation device slidably engaging the interior surface of the tube in an essentially fluid-tight manner and having an axial orifice on the longitudinal axis of the tube that is in fluid flow communication with a flow-restriction channel, said flow-restriction channel being off-set from the longitudinal axis of the tube, said flow-restriction channel having a convoluted path with at least two axially-oriented sections with opposed directions of fluid flow, said axial orifice being in fluid flow communication with the first chamber and said flow-restriction channel being in fluid flow communication with the second chamber;

(b) ordering the phases of the sample concentrically by rotating the tube around its longitudinal axis;

(c) while the phases are ordered, reducing the volume of the first chamber by movement of the separation device within the tube, that phase of the liquid located axially within the first chamber flowing into the axial orifice and passing through the flow-restriction channel into the second chamber; and (d) deriving phase-separation information from the location of the interface between the phases and controlling the reduction of the volume of the first chamber on the basis of the phase-separation information.

In a preferred embodiment of the method of the invention, the flow-restriction channel permits flow of liquid from the first chamber to the second chamber during step (c) but restricts flow of liquid at other times.

In another embodiment, the second chamber is formed as the separation device is moved within the tube.

The present invention additionally provides a method of partitioning a pre-selected phase of a sample of liquid having a plurality of phases of differing densities, comprising the steps of:

(a) containing said sample of liquid in a first chamber of a linear tube, said tube having a second chamber that is separated from the first chamber by a separation device, said second chamber being free of the liquid, said separation device slidably engaging the interior surface of the tube in an essentially fluid-tight manner and having an axial orifice on the longitudinal axis of the tube that is in fluid flow communication with a flow-restriction channel, said flow-restriction channel being off-set from the longitudinal axis of the tube, said flow-restriction channel having a convoluted path with at least two axially-oriented sections with opposed directions of fluid flow, said axial orifice being in fluid flow communication with the first chamber and said flow-restriction channel being in fluid flow communication with the second chamber; and (b) ordering the phases of the sample by subjecting the tube to centrifugal force.

The present invention also provides a separation device adapted to slidably engage the interior surface of a chamber in a linear tube in an essentially fluid-tight manner, said separation device having an axial orifice on the longitudinal axis thereof in fluid flow communication with a flow-restriction channel, said flow-restriction channel being off-set from the longitudinal axis of the separation device, said flow-restriction channel having a convoluted path with at least two axially-oriented sections with opposed directions of fluid flow, said axial orifice and said flow-restriction channel providing fluid flow communication between a first side of the separation device and a second side of the separation device.

In addition, the present invention provides a tube having a sealable opening on at least one end and a separation device located within the tube, said separation device separating a first chamber from a second chamber within said tube, said separation device slidably engaging the interior surface of the tube in an essentially fluid-tight manner and having an axial orifice on the longitudinal axis of the tube in fluid flow communication with a flow-restriction channel, said flow-restriction channel being off-set from the axis of the tube and having a convoluted path with at least two axially-oriented sections with opposed directions of fluid flow, said axial orifice being in fluid flow communication with the first chamber and said flow-restriction channel being in fluid flow communication with the second chamber, said tube and separation device providing means to insert liquid into the first chamber.

In embodiments of the invention, the flow-restriction channel is a single continuous channel, especially a single continuous channel that substantially encircles the longitudinal axis of the tube.

In other embodiments of the invention, the convoluted path conforms to the surface of a cone.

In further embodiments of the invention, the second chamber is an incipient chamber that forms as the separation device is moved along the tube.

DESCRIPTION OF THE DRAWINGS

The invention will be described with particular reference to the drawings in which.

Figure 1:
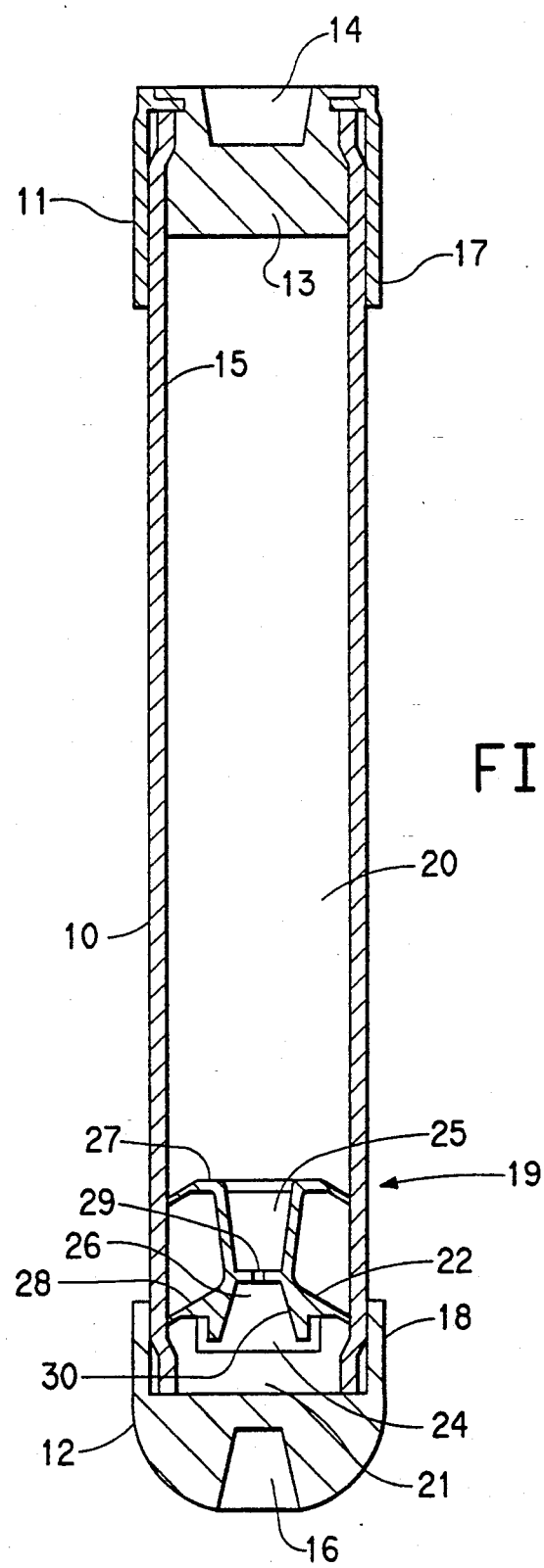
FIG. 1 is a schematic representation of a cross-sectional area of one embodiment of the separation device in a tube.
Figure 2:
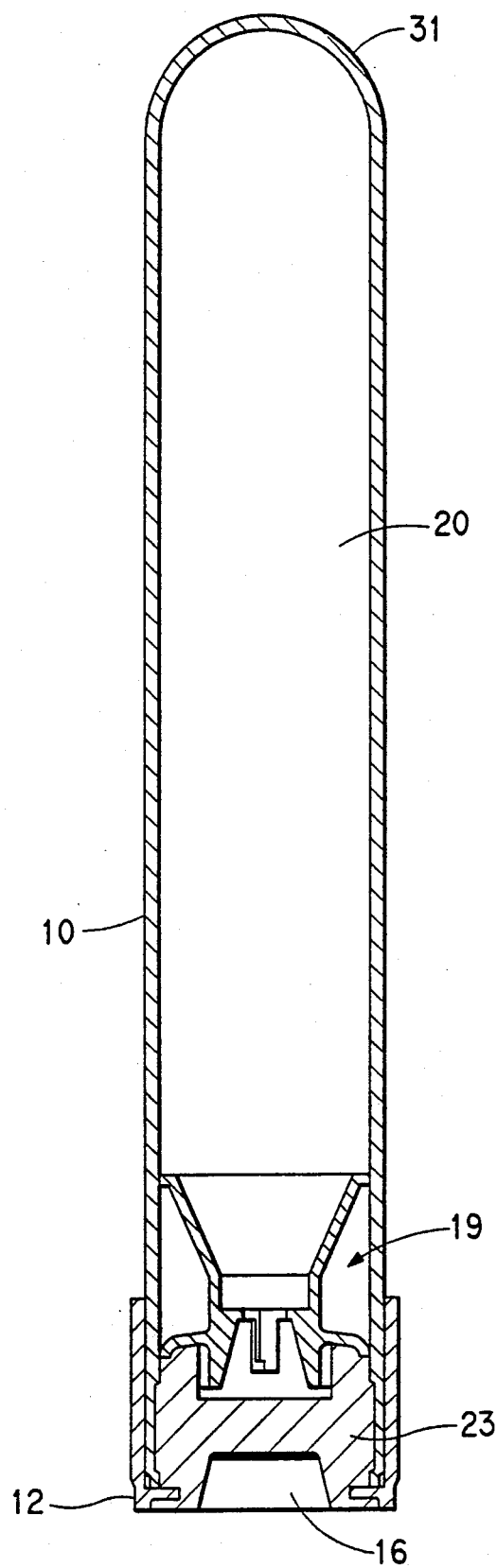
FIG. 2 is a schematic representation of a cross-sectional area of another embodiment of the separation device in a tube.
Figure 3:
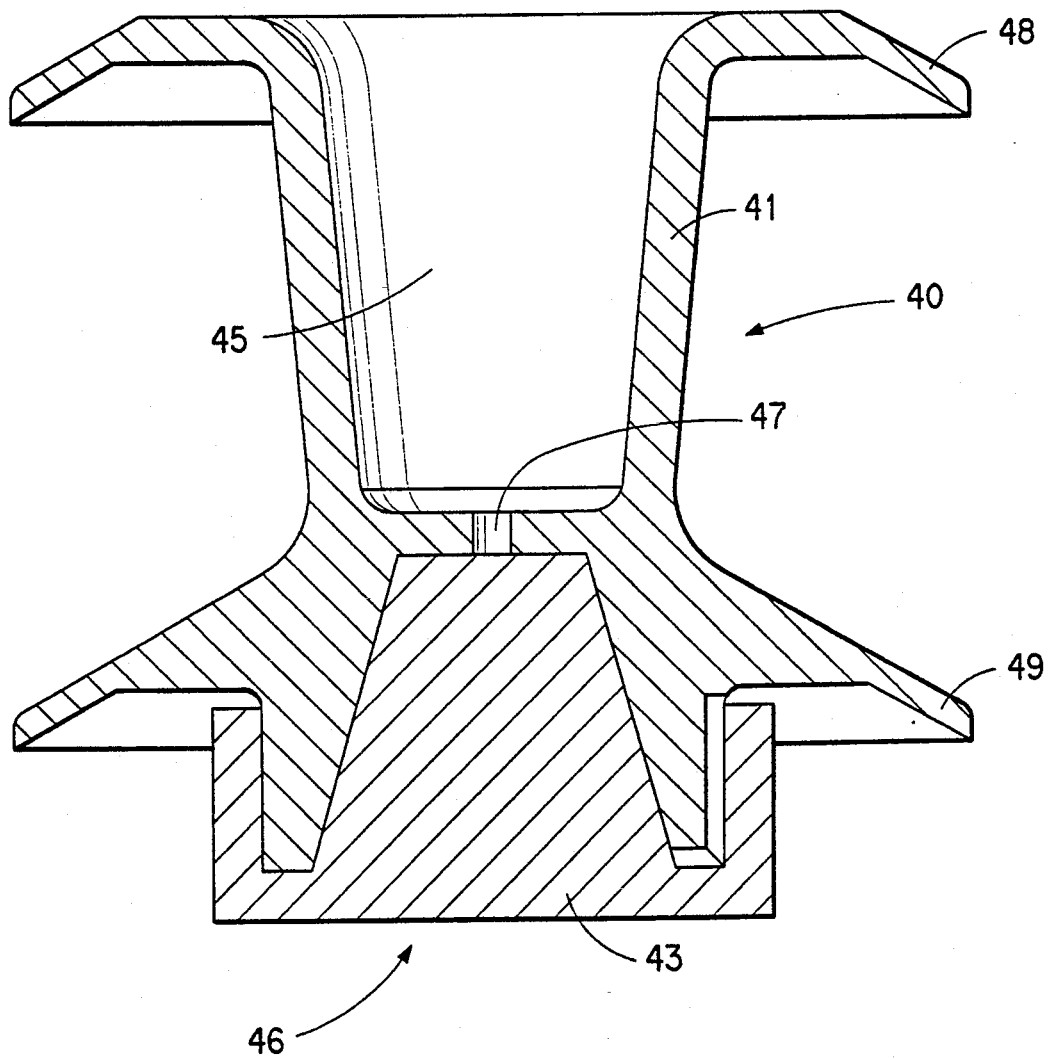
FIG. 3 is a schematic representation of a cross-sectional area of a separation device.
Figure 4:
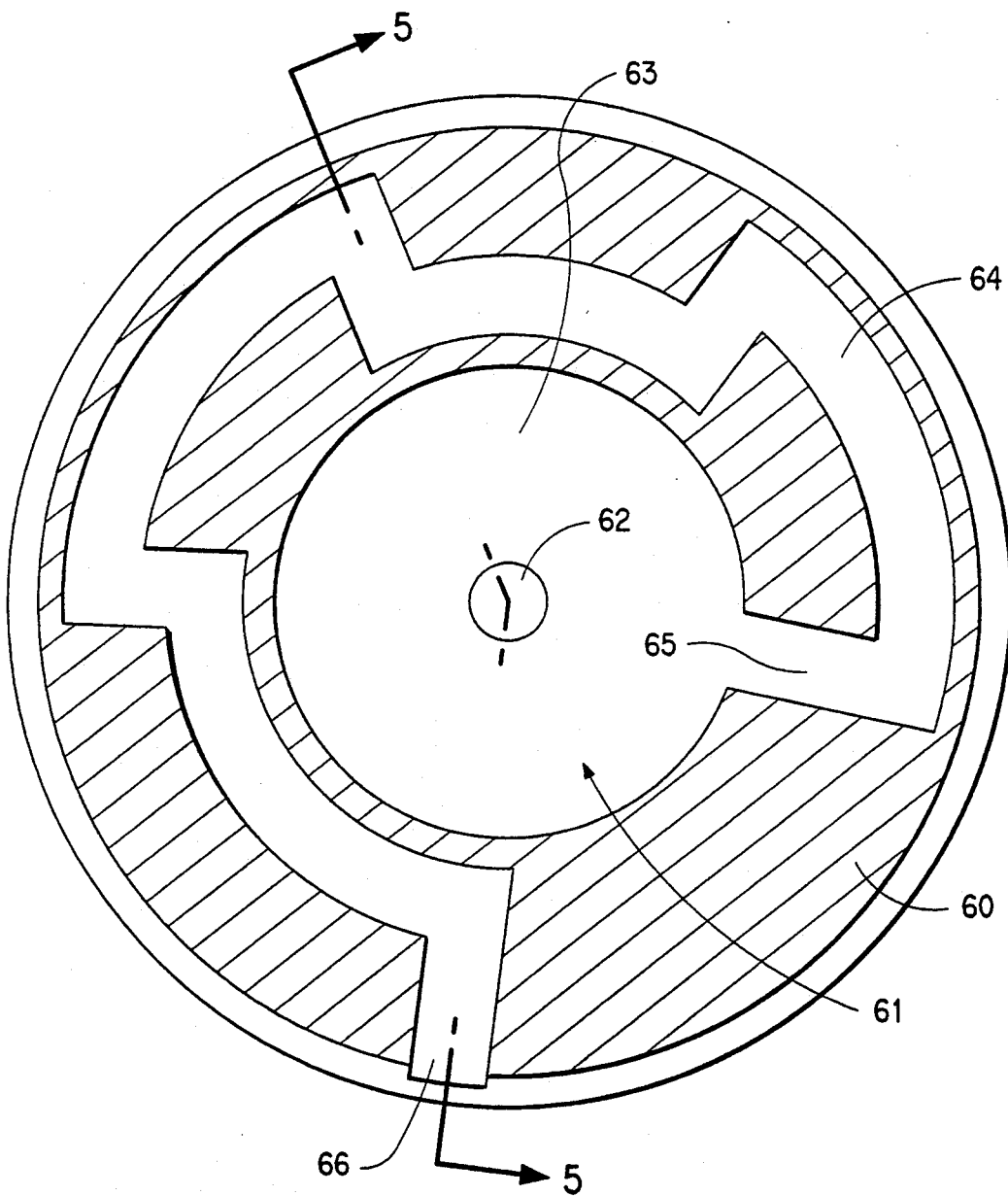
FIG. 4 is a schematic representation of a plan view of a tortuous path in the separation device.

The embodiments shown in FIG. 3 and FIG. 4 particularly relate to the embodiment shown in FIG. 1. Similarly, the embodiments shown in FIG. 6 and FIG. 7 particularly relate to the embodiment shown in FIG. 2.

DETAILED DESCRIPTION

Referring to FIG. 1, tube 10 (which may also be known as or referred to as a vial) is shown as having a first end cap 11 and a second end cap 12. As shown, the end caps are of different construction. Tube 10 has a substantially constant diameter, and constant cross-section, throughout a major portion of its length. First end cap 11 is comprised of a plug 13 having recess 14. Plug 13 fits inside tube 10 and forms a fluid and vacuum tight seal with the inner surface 15 of tube 10, so as to form a fluid tight closure with tube 10. First end cap 11 also has rim 17 that fits tightly onto the outside of tube 10. In addition, the exposed end of first end cap 11 is shown as having a flat end, which could be used to stand the tube in a vertical position. In contrast, second end cap 12 is shown as having a rounded exposed end. The shape of the end of end caps 11 and 12 is not critical to the invention; the material of construction is more important, as will become apparent, for penetration of needles and probes during use of the tubes.

Second end cap 12 is shown as having recess 16, which is axially located in the end cap. In addition, second end cap 12 has rims 18 which fit over the end of tube 10 to form a fluid and gas tight seal therewith. It will be appreciated that there are variations in the type of end cap that may be used. In embodiments, the end cap is accompanied by a stopper or plug, with the stopper or plug providing the fluid and gas tight seal and the end cap being for protection and/or to retain the stopper or plug in place.

The separation device in tube 10 is generally indicated by 19. Separation device 19 divides the space within tube 10 into first chamber 20 and second chamber 21; it is to be understood that in embodiments of the invention, end cap 12 contacts and seats with separation device 19 such that second chamber 21 is in effect an incipient chamber which forms into chamber 21 on movement of separation device 19 within tube 10. Separation device 19 is comprised of separation shell 22 and plug 24. Separation shell 22 has a first shell recess 25 disposed towards first chamber 20 and second shell recess 26 disposed towards second chamber 21; first shell recess 25 may contain a filter (not shown). Separation shell 19 also has first flange 27 and second flange 28, which in the embodiment shown are non-planar curved surfaces that extend to and are in sliding engagement with inner wall 15 of tube 10, and form an effective fluid tight seal therewith; flanges of other shapes may be used. While two flanges are shown, and are preferred, it is believed that at least one flange is required. Plug 24 is located in second shell recess 26. The inner surface 30 has a convoluted path formed in the surface thereof which, in conjunction with the surface of plug 24, forms a channel (not shown, see FIG. 4) that is in fluid flow communication between opposite ends of plug 24. Separation shell 19 is shown as having an axial orifice 29 for flow of fluid.

The space between first flange 27 and second flange 28, either between the separation device 19 and the inner wall 15 or the region in first recess 25, is used for monitoring of the separation process. While optical monitoring of the process is a preferred method, other methods e.g. infrared and ultrasonic, may be used.

Plug 24 would normally be made from an elastomeric material, especially a self-sealing elastomeric material. As will be apparent from the disclosure herein, in one mode of operation, especially the embodiment shown in FIG. 2, a needle is inserted through second end cap 12 (via recess 16), through plug 24 for the insertion of liquid into first chamber 20. Plug 24 has additional requirements with respect operation of the method described herein, during movement of the separation device 19 within tube 10.

The materials of construction of the end caps and plugs or stoppers in the embodiments of FIG. 1, and FIG. 2 and other embodiments, will particularly depend on the method of operation. End caps will normally be relatively rigid plastic, depending on whether penetration by needles is required. Plugs or stoppers may be rigid or elastomeric, including self-sealing elastomeric, depending on whether a needle is passed through the plug prior to centrifugation thereby requiring self-sealing material. The self-sealing materials referred to herein are known in the art of blood collection tubes.

FIG. 2 shows an embodiment that is the same as that shown in FIG. 1, except that tube 10 has only second end cap 12 i.e. first end cap 11 has been replaced by using a tube having only one open end, at the location of second end cap 12. End 31 is integral with the remainder of tube 10. In addition, second end cap 12 holds stopper 23 in position at the end of tube 10. Stopper 23 is shown as snugly fitting separation device 19, such that chamber 21 (not shown in FIG. 2 but shown elsewhere) has become an incipient chamber.

FIG. 3 shows a separation device, generally indicated by 40; separation device 40 is the same as separation device 19, but shown in more detail. Separation device 40 has a separation shell 41 with plug 43. Plug 43 is located in second axial recess 46, which is at the opposite end of separation shell 40 from first axial recess 45. A channel (not shown) with a convoluted path is located at the interface between plug 43 and the surface of separation shell 40 that defines the shape of second axial recess 46. Access channel 47 is located in separation shell 40 between first axial recess 45 and second axial recess 46.

Separation shell 40 also has first flange 48 and second flange 49. Each of first flange 48 and second flange 49 are intended to contact the inner surface of a tube and to be in sliding engagement therewith, to the extent that no significant amount of liquid will pass by first flange 48 and second flange 49 and cause contamination of separated phases.

FIG. 4 shows a plan view of the channel with a convoluted path located on separation shell 40 of FIG. 3, at the interface between second axial recess 46 and the separation shell. The surface 60 of second axial recess, generally indicated by 61, has central axial orifice 62, manifold 63 and channel 64. Channel 64 has entrance 65 and exit 66, and is shown as being a single continuous channel between entrance 65 and exit 66. However, in the embodiment shown, channel 64 has eight right-angled elbows so that channel 64 twists and turns around the surface 60 of second axial recess 61. A convoluted path is thus formed, and the convoluted path has sections that are generally in each of a radial direction, an axial or longitudinal direction and circumferentially oriented. It is believed that the path requires axially oriented sections with opposed directions of flow, and preferably such that the longitudinal axis is substantially encircled, to inhibit reverse flow in the channel, as discussed hereinafter; radially oriented sections are believed to be less important with respect to flow of fluid or inhibition thereof.

Figure 5:
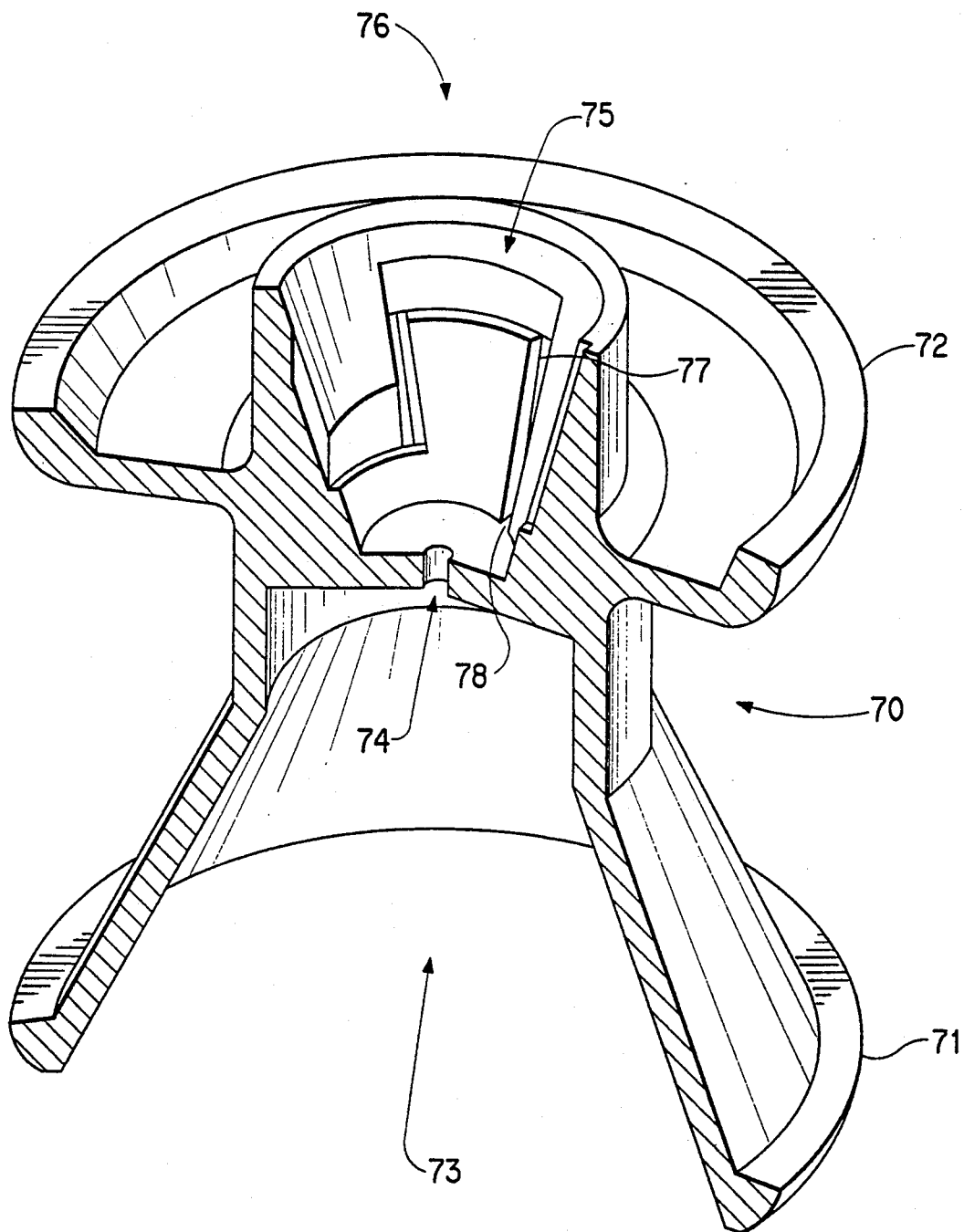
FIG. 5 is a schematic representation of a section of a separation device taken through line 5—5 of FIG. 4.

FIG. 5 shows a section of the separation device along the line 5—5 of FIG. 4. Separation device 70 has a first flange 71 and a second flange 72. First axial recess 73 is in fluid flow communication with axial orifice 74 that is located on the longitudinal axis of separation device 70. Plug 75 in second axial recess 76 is shown in cross-section. Channel 77 in plug 75 has a convoluted path, commencing with channel entrance 78 which is in fluid flow communication with axial orifice 74. As shown in the drawing, channel 77 proceeds from channel entrance 78 in an axial direction, turns at right angles and proceeds circumferentially for a distance and then turns into an axial direction that is opposed to the axial direction connected to channel entrance 78. Channel 77 is then shown as proceeding further in a circumferential manner and then in an axial direction.

Figure 6:
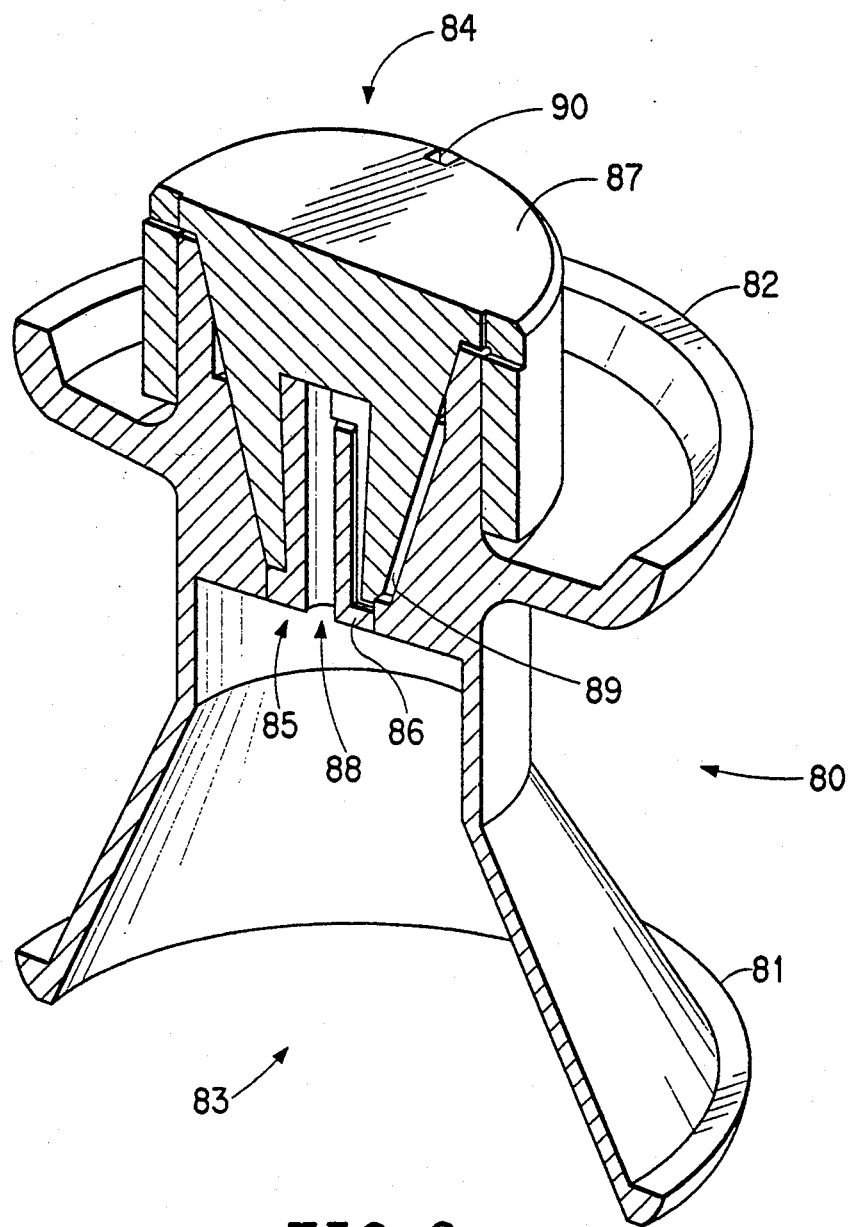
FIG. 6 is a schematic representation of a section of another embodiment of a separation device.

FIG. 6 shows another embodiment of a separation device. Separation device 80 has first flange 81 and second flange 82, as well as first axial recess 83 and second axial recess 84. In this embodiment, there is no axial channel per se formed between first axial recess 83 and second axial recess 84, but rather opening 85. Opening 85 has insert plug 86 therein, insert plug 86 being recessed into and seated with plug 87 in second axial recess 84. Insert plug 86 has axial channel 88 located on the longitudinal axis of separation device 80. Axial channel 88 is showing as extending for the full length of insert plug 86, before proceeding through two right-angled bends to be axially oriented in the opposed direction and then in a radial direction. Axial channel 88 then connects with plug channel 89 formed at the surface of plug 87, and finally exits at exit 90.

Figure 7:
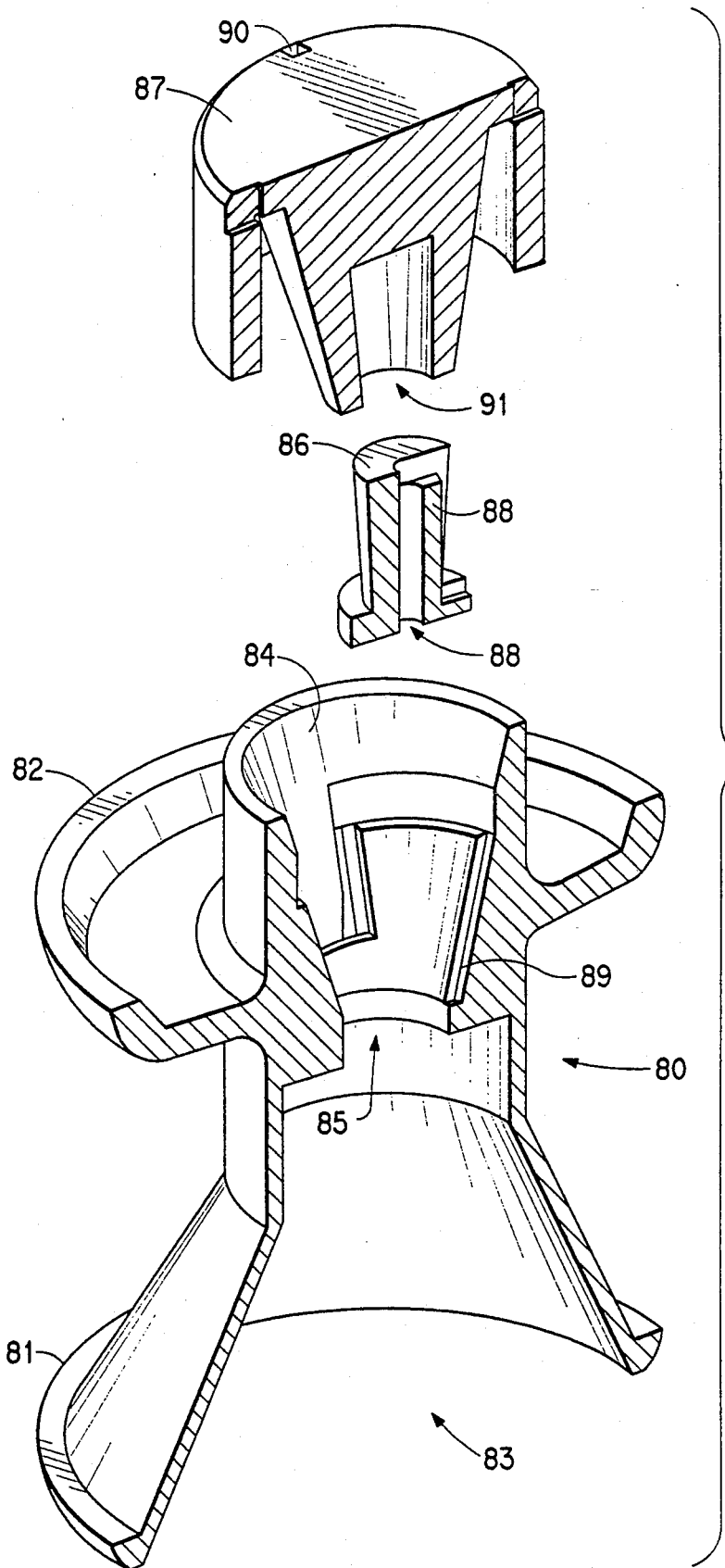
FIG. 7 is a schematic representation of an exploded view of the separation device of FIG. 6.

FIG. 7 shows an exploded view of the embodiment of FIG. 6. Separation device 80 has first axial recess 83 and second axial recess 84, with opening 85 therebetween. Opening 85 is adapted to accept plug 87. Insert plug 86 fits into and seats in plug recess 91 in plug 87. Insert plug 86 has axial channel 88 located on the longitudinal axis of separation device 80. Axial channel 88 is showing as extending for the full length of insert plug 86, before proceeding through two right-angled bends to be axially oriented in the opposed direction and then in a radial direction. Plug channel 89 is formed in separation device 80 at second axial recess 84.

In operation, a sample of liquid having phases of differing densities e.g. blood, is placed in the tube; the operation of the method of the invention will generally be described herein with reference to separation of blood into a cell fraction and a non-cellular fraction. The blood is inserted into first chamber 20. In the embodiment of FIG. 1, this may be done by removing first end cap 11 and inserting the blood. However, for safety reasons, blood is normally drawn into first chamber 20, as a consequence of having a vacuum inside first chamber 20, using a needle. This may be done by injection through first end cap 11 and plug 13 directly into first chamber 20 in the embodiment of FIG. 1. Alternatively, for the embodiment of FIG. 2, blood is drawn in to chamber 20 through a needle inserted through second end cap 12, through plug 24 and into chamber 20; in this embodiment, the material from which plug 24 is fabricated must be selected so as to permit the needle to pass through the plug under reasonable force and be self-sealing on withdrawal of the needle, and to provide sufficient resistance to the probe during movement of the separation device along the tube without distending to plug the channel. Injection through first end cap 11 is preferable as it overcomes potential contamination problems associated with withdrawal of the needle through second end cap 12 and drops of blood becoming deposited in second chamber 21 or in recess 16 after the needle is withdrawn; droplets in recess 16 would contaminate the probe subsequently inserted to obtain movement of the separation shell 19 within tube 10 in a single-ended tube i.e. a tube with only one end cap, but not in a double-ended tube i.e a tube with end caps on both ends, as in the latter the needle is passed through one end cap and the probe is passed through the other end cap.

The separation device is particularly intended for use in an axial centrifuge e.g. an axial centrifuge of the type described in the aforementioned U.S. Pat. No. 4 828 716. The separation device is rotated about its longitudinal axis to effect phase separation. When separation is complete, the high viscosity, concentrated, clotted cells are located near the tube wall and the lower viscosity serum (and any air or other gases) are located closer to the longitudinal axis. A probe then penetrates second end cap 12 and contacts and is resisted by second plug 24. Further force by the probe causes the separation device to move along tube 10, thereby decreasing the volume of first chamber 20. This decrease in volume results in the material located on the longitudinal axis flowing through access channel 47, along the convoluted path located at the interface between plug 24 and separation shell 19 and into second chamber 21. Air or other gaseous matter is the first to flow into second chamber 21, followed by serum. An optical sensor is located exterior to the tube and is able to monitor the separation device as it moves along the tube. The sensor passes light through that part of shell recess 25. When blood cells approach shell recess 26 and are detected, the movement of the probe, and hence the separation device 19, ceases, and thus the blood cells do not enter second chamber 21. The probe is withdrawn while the tube is still being rotated about its axis, with the result that the probe does not become contaminated by the sample in the tube. Thus, it is believed that the probe may be used on a subsequent sample without cross-contamination of samples.

The tube is made of an optically transparent material e.g. glass or Selar ® polyamide, which is manufactured by E.I. du Pont de Nemours and Company of Wilmington, Del. U.S.A. Other optically transparent materials may be used, prime requirements being acceptable transparency and sufficient strength to withstand the forces applied in a centrifugation process. In addition, the tube must be capable of retaining a vacuum, a capability of retention of vacuum for a period of about 2 years being preferred. Tubes or vials of acceptable properties are known and used in the collection and processing of blood. The separator shell may be moulded from thermoplastic or other polymers, a prime requirement being that the polymer not have adverse effects on the properties and characteristics of the blood and the components thereof. The separation device needs to be optically transparent, if optical means are to be used for the monitoring and control of the method of separation of the liquid into phases. Otherwise, a material suitable for the particular monitoring method is required. In addition, the separation device needs to provide an adequate fluid seal against the side of the tube in which it is located, and be capable of being fabricated into the shape of the separation device. An example of a suitable material is polypropylene.

The material used in the fabrication of the plugs will depend in particular on the tube being used. For a single ended tube, it is essential that a needle be able to penetrate through the plugs so that liquid e.g. blood can be introduced into the first chamber; the material needs to be self-sealing on withdrawal of the needle and not core i.e. plug the needle with a portion of the plug. Subsequently, if a probe is used to move the separation device along the tube, then the material of the plug must be able to provide sufficient resistance to the probe to obtain movement of the separation device, while at the same time not causing distortion or the like of the plug to the extent that the channels required for fluid flow become blocked. Ethylene/vinyl acetate polymer compositions have been found to be acceptable, including Elvax ® 250, 260, 450 and 550 polymer compositions available from E.I. du Pont de Nemours and Company, but other compositions will become apparent to persons skilled in the art. If a double ended tube is used, there is no need for a needle to penetrate the plug, and the requirements on the plug are less stringent.

The end caps need to be made from a self-sealing material, especially a self-sealing elastomeric material. Examples of such materials are known in the art.

The convoluted path of channel 64 is important with respect to the flow of material through the channel. It is preferable that fluid not flow back from second chamber 21 into first chamber 20 after the axial centrifuging of the tube has ceased, but it is more important that fluid not continue to flow, albeit intermittently, from first chamber 20 into second chamber 21. In particular, it is important that in-use handling, including inverting, laying on side, dropping, shaking and tipping of the tube, does not result in flow of fluid in either direction, especially not flow of the cell fraction from chamber 20 into chamber 21. The convoluted path accomplishes has characteristic, when in dimensions suitable for the fluid being separated. The channel preferably has both a circumferentially-oriented section and a longitudinally-oriented section. As discussed above, at least one reversal of direction axially and a substantially complete encirclement of the longitudinal axis offset from that axis should be used to prevent flow from sedimentation of cells, regardless of tube orientation, but two or more changes of axial direction are preferred; an axial spiral has been found to give unacceptable results. In addition, because a higher pressure is required to force concentrated, clotted cells through the flow channel than for serum, it is possible to provide a channel of sufficiently small area and sufficient length to permit the flow of serum but inhibit the flow of cell fractions.

The convoluted path of the channel is described herein as preferably located on the surface of a cone, primarily for reasons of ease of manufacture. However, the channel could be located on surfaces of different shape e.g. cylinders, spheres or the like, but such channels may be substantially more difficult to manufacture in a consistent manner.

The separation shell and plugs are fabricated separately for ease of manufacture. In the embodiments in the drawings, the entire flow channel has been shown to be fabricated in the surface of the separation shell, which is preferred for ease of manufacture but, in other embodiments, it could be fabricated as part of the plug. As noted above, conical mating surfaces, as shown, are preferred.

The separation device of the present invention has a minimal number of independent parts, resulting in few critical mating surfaces and connections, for improved consistency and reliability from tube to tube. In addition, the separation device is of a passive design, with no movable parts. The separation device has a longitudinally located axial channel for effective separation of serum from blood cells, and provides maximum serum yield with minimal air retention in the first chamber 20. The chambers are essentially free of sharp edges and discontinuous surfaces, or the like, that might promote cell trauma or retention of a clot. The single flow channel is believed to be important, since multiple channels tend to permit cross-flow between chambers and result in inferior separation. The channel should be of small cross-sectional area, especially so that only a small portion of the separated phase is retained within the channel. The flow path is long and convoluted or tortuous, resulting in a long flow distance within a relatively small separation device, which also maximizes the volume available within the chambers for blood component collection and storage.

A filter may be used in first shell recess 25 to filter fluid passing through that recess to the axial orifice. For example, platelets could be filtered from the blood fraction passing through the axial orifice.

It is understood that the tubes may contain anticoagulants or clot activators, as is known in the art.

Although the tube and separation device have been described herein with particular reference to axial centrifugation, at least some tubes and separation devices described herein are also capable of being used in conventional centrifuges. It is to be understood, however, that the separation device may not function in the manner described herein even though the tube containing the separation device is usable.

The present invention is illustrated by the following examples:

EXAMPLE I

To illustrate separation of blood into components using the separator device of the present invention, two samples of blood were collected by conventional means and then transferred into a single ended tube having a separation device as illustrated herein. The plug in the separation device was fabricated from Elvax 550 ethylene/vinyl acetate copolymer and the separation device had centre line sampling as is illustrated. The blood was allowed to clot for one hour. The tubes were then placed in an axial centrifuge and, after the cellular and non-cellular components had become ordered, the separation device was moved down the tube using a probe; the probe was stopped prior to the cellular component entering the separation device. A sample of the non-cellular component (serum) was removed and analyzed in the laboratory of the Ottawa Civic Hospital, Ottawa, Ontario.

As a comparison, two samples of blood were taken using commercially available tubes viz. Becton Dickinson vacutainer tubes, and after being allowed to clot for one hour were centrifuged in a conventional swinging bucket centrifuge. A sample of the non-cellular component (serum) was removed and analyzed at the same time as the above samples in the laboratory of the Ottawa Civic Hospital, Ottawa, Ontario.

The blood was obtained from the same person, on the same day.

The results obtained were as follows:

TABLE I

|  | Run 1 | Run 2 | Run 3 | Run 4 |
|---|---|---|---|---|
| Blood volume (mL) | 8.2 | 8.5 | 8.3 | 8.5 |
| Serum volume (mL) | 2.9 | 2.9 | 3.5 | 3.6 |
| Relative serum yield (%) | 61 | 59 | 80 | 79 |
| Serum quality | good | good | good | good |
| Serum colour | clear | clear | — | — |
| WBC ($\times 10^6$/L) | 0 | 0 | 0.1 | 0.1 |
| Platelet count ($\times 10^9$/L) | 5 | 6 | 4 | 4 |
| RBC count ($\times 10^{12}$/L) | 0 | 0 | 0 | 0 |
| Hemoglobin (mg/%) | 1 | 1 | 1 | 1 |
| Sodium (mM/L) | 146 | 145 | 146 | 145 |
| Potassium (mM/L) | 4.4 | 4.3 | 4.3 | 4.1 |
| Chloride (mM/L) | 107 | 108 | 107 | 107 |
| Glucose (mM/L) | 4.4 | 4.1 | 3.9 | 3.5 |
| Urea (mM/L) | 6.8 | 6.7 | 6.7 | 6.7 |
| Creatinine ($\mu$M/L) | 104 | 108 | 104 | 104 |
| Urate ($\mu$M/L) | 283 | 281 | 286 | 280 |
| Calcium (mM/L) | 2.4 | 2.4 | 2.37 | 2.34 |
| Albumin (g/L) | 43 | 43 | 43 | 43 |
| Total Protein (g/L) | 72 | 72 | 71 | 71 |
| phosphate (mM/L) | 1.05 | 1.05 | 1.06 | 0.97 |
| ALT (Units/L) | 24 | 23 | 22 | 24 |
| AST (Units/L) | 23 | 22 | 24 | 23 |
| Alkaline phosphatase (Units/L) | 89 | 89 | 89 | 89 |
| Cholesterol (mM/L) | 5.2 | 5.4 | 5.2 | 5.2 |
| Total bilirubin ($\mu$M/L) | 10 | 10 | 10 | 9 |
| Direct bilirubin ($\mu$M/L) | 2 | 2 | 2 | 2 |
| Gamma GT (Units/L) | 23 | 24 | 24 | 23 |
| LDH-L (Units/L) | 153 | 142 | 142 | 155 |
| Creatinine kinase (Units/L) | 94 | 93 | 90 | 92 |
| Magnesium (mM/L) | 0.89 | 0.88 | 0.89 | 0.88 |
| Carbon dioxide (mM/L) | 31 | 32 | 33 | 32 |
| Triglycerides (mM/L) | 1.75 | 1.75 | 1.70 | 1.71 |

Note:
Runs 3 and 4 are the comparative runs.

The values given in the above table, and the variation in the results obtained, are within normal tolerance variation for such tests. This shows that the separation device, tube and method of the invention give effective separation of blood components. The operation of the probe can be, and has been, adjusted to give a higher serum yield.

We claim:

1. A method of partitioning a pre-selected phase of a sample of liquid having a plurality of phases of differing densities, comprising the steps of:

(a) containing said sample of liquid in a first chamber of a linear tube, said tube having a second chamber that is separated from the first chamber by a separation device, said second chamber being free of the liquid, said separation device slidably engaging the interior surface of the tube in a fluid-tight manner and having an axial orifice on the longitudinal axis of the tube that is in fluid flow communication with a flow-restriction channel, said flow-restriction channel being off-set from the longitudinal axis of the tube, said flow-restriction channel having a convoluted path with at least two axially-oriented sections with opposed directions of fluid flow, said axial orifice being in fluid flow communication with the first chamber and said flow-restriction channel being in fluid flow communication with the second chamber;

(b) ordering the phases of the sample concentrically by rotating the tube around its longitudinal axis;

(c) while the phases are ordered, reducing the volume of the first chamber by movement of the separation device within the tube, that phase of the liquid located axially within the first chamber flowing into the axial orifice and passing through the flow-restriction channel into the second chamber; and (d) deriving phase-separation information from the location of the interface between the phases and controlling the reduction of the volume of the first chamber on the basis of the phase-separation information.

2. The method of claim 1 in which the flow-restriction channel permits flow of liquid from the first chamber to the second chamber during step (c) but restricts flow of liquid at other times.

3. The method of claim 1 in which the flow-restriction channel is a single continuous channel.

4. The method of claim 3 in which the second chamber is an incipient chamber that forms as the separation device is moved along the tube.

5. The method of claim 4 in which the single continuous channel substantially encircles the longitudinal axis of the tube.

6. The method of claim 3 in which the convoluted path conforms to the surface of a cone.

7. The method of claim 3 in which the tube is a single-ended tube, with an end cap on only one end of the tube.

8. The method of claim 3 in which the tube is a double-ended tube, with an end cap on both ends of the tube.

9. A method of partitioning a pre-selected phase of a sample of liquid having a plurality of phases of differing densities, comprising the steps of:

(a) containing said sample of liquid in a first chamber of a linear tube, said tube having a second chamber that is separated from the first chamber by a separation device, said second chamber being free of the liquid, said separation device slidably engaging the interior surface of the tube in a fluid-tight manner and having an axial orifice on the longitudinal axis of the tube that is in fluid flow communication with a flow-restriction channel, said flow-restriction channel being off-set from the longitudinal axis of the tube, said flow-restriction channel having a convoluted path with at least two axially-oriented sections with opposed directions of fluid flow, said axial orifice being in fluid flow communication with the first chamber and said flow-restriction channel being in fluid flow communication with the second chamber; and (b) ordering the phases of the sample by subjecting the tube to centrifugal force.

10. The method of claim 9 in which the flow restriction channel is a single continuous channel.

11. The method of claim 10 in which the tube is a single-ended tube, with an end cap on only one end of the tube.

12. The method of claim 10 in which the tube is a double-ended tube, with an end cap on both ends of the tube.

* * * * *